(12) United States Patent
Evans

(10) Patent No.: US 6,596,007 B2
(45) Date of Patent: Jul. 22, 2003

(54) DUAL COIL ELECTROMAGNET USING RECTILINEAR CROSS-SECTION CORE ELEMENTS IN A TATTOO APPARATUS

(76) Inventor: Todd Matthew Evans, 3355 N. Wild Daisy Pl., Tuc., AZ (US) 85750

( * ) Notice: Subject to any disclaimer, the term of this patent is extended or adjusted under 35 U.S.C. 154(b) by 0 days.

(21) Appl. No.: 09/867,877

(22) Filed: May 30, 2001

(65) Prior Publication Data

US 2003/0050657 A1 Mar. 13, 2003

(51) Int. Cl.[7] ............................................. A61B 17/32
(52) U.S. Cl. ..................................................... 606/186
(58) Field of Search ................................. 606/181, 186, 606/185; 81/9.22; 30/362

(56) References Cited

U.S. PATENT DOCUMENTS

| | | | | |
|---|---|---|---|---|
| 3,659,124 A | * | 4/1972 | Lathrop | |
| 3,743,870 A | * | 7/1973 | Hunt | |
| 4,159,659 A | * | 7/1979 | Nightingale | 606/186 |
| 4,204,438 A | * | 5/1980 | Binaris et al. | 81/9.22 |
| 4,521,957 A | * | 6/1985 | McLeod | 29/609 |
| 5,054,339 A | * | 10/1991 | Yacowitz | 81/9.22 |
| 5,092,027 A | * | 3/1992 | Denner | 29/607 |
| 5,401,242 A | * | 3/1995 | Yacowitz | 604/48 |
| 5,551,319 A | * | 9/1996 | Spaulding et al. | 81/9.22 |
| 6,282,987 B1 | * | 9/2001 | Moniz | 81/9.22 |

* cited by examiner

Primary Examiner—Michael J. Milano
Assistant Examiner—Paul A Roberts

(57) ABSTRACT

Electromagnetic coils having rectilinear cross-section core elements and an armature bar having a rectilinear cross-section are described in a handheld tattoo apparatus. This results in increased vibrational smoothness as sensed by the tattoo artist.

5 Claims, 2 Drawing Sheets

DUAL COIL ELECTROMAGNET USING RECTILINEAR CROSS-SECTION CORE ELEMENTS IN A TATTOO APPARATUS

BACKGROUND OF THE INVENTION

Dual coil electromagnets are used in tattoo machines and are well known in the art. In particular, the dual coil machines operating on a direct current power supply follow the patents of Wagner, U.S. Pat. No. 768,413 and Waters, U.S. Pat. No. 1,724,812. Both of these machines teach dual coils that are excited by a direct current power supply. This electrical excitation produces a magnetic field that attracts a spring-biased, moving armature bar toward the coils. The motion of the armature bar opens a switch in the electrical circuit causing the current and the magnetic field to decay, thereby allowing the bias spring to return the armature bar to its original position. This closes the switch which completes the circuit again and the process repeats itself This causes a vibration of the armature bar. This motion is coupled to the tattoo needle, causing it to vibrate axially. The needle can then be used to penetrate the skin and deposit ink, as is well known in the art. The end of each coil opposite the moving armature bar is attached to a connecting bar that is usually also a structural element.

DESCRIPTION OF THE INVENTION

Figure 1:
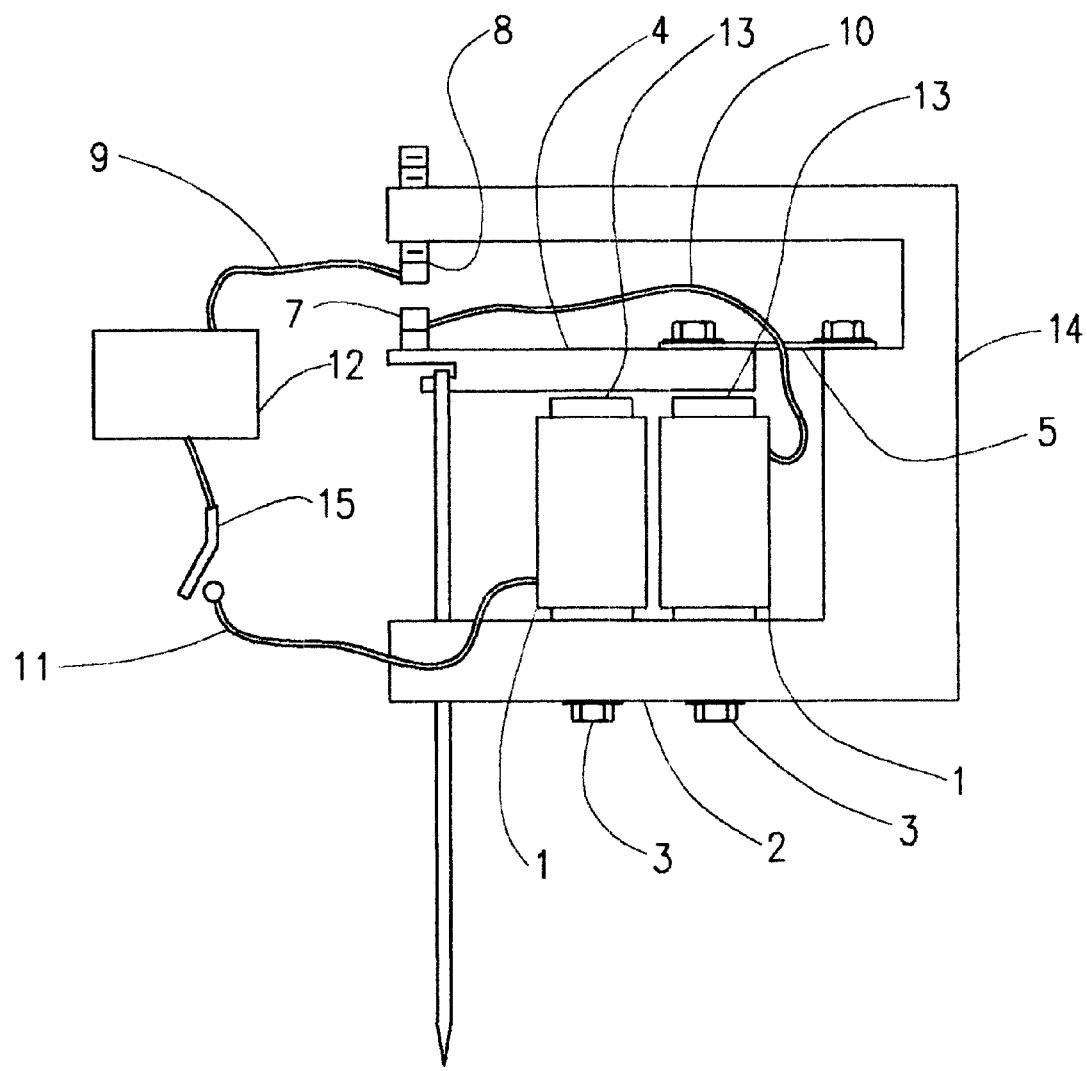
FIG. 1 shows a side elevation of the invention.

As shown in FIG. 1, the invention uses two coils 1 placed side-by-side and attached by means of threaded fasteners 3 to a connecting bar 2 that is part of a frame that is a supporting structural element. The connecting bar 2 is made of a magnetic material such as iron or steel and is rectilinear in cross-section. An armature bar 4 is supported by a flat bias spring 5 so that it is suspended over the ends of the cores 13 of the coils 1. The flat bias spring is attached to the frame 14. The armature bar 4 is of rectilinear cross section and is made of a magnetic material such as iron or steel. An air gap exists between the ends of the cores 13 and the armature bar 4. In the first position, shown in FIG. 1, the coils are not energized. The frame 14 supports an upper electrical contact 8 that is axially adjustable and that is electrically insulated. The upper electrical contact 8 is connected to an electrical power supply 12 by an electrical wire 9. A lower electrical contact 7 is attached to the armature bar 4 and is electrically insulated from it. The lower contact 7 is connected to an electrical wire 10 that is connected to the electrical windings of the coils. The return wire 11 from the coils 1 is connected to an electrical switch 15 that is connected to the other pole of the power supply 12. This circuitry is well known in the art. When the switch 15 is closed, current flows through the closed contacts 7 and 8 and through the coils 1, generating an axial magnetic field in the core 13 of each coil 1. The coils are wound and electrically connected such that the direction of the magnetic fields in each are in opposite directions. This causes a magnetic flux path from the core of one coil, through the armature bar 4 (in the portion between the core ends), axially through the core of the second coil, through the connector bar 2 (in the portion between the core ends), and axially back through the coil where it started. This continuous magnetic flux path causes the armature bar 4 to be attracted to the coil cores 13 and to move downward as shown in FIG. 1. This motion also moves the lower contact 7 downward which opens the electrical circuit causing the current and magnetic field to decay. The bias spring 5 overcomes the decaying magnetic attraction and returns the armature bar 4 to its first position. The lower contact 7 contacts the upper contact 8 and current flows again, recreating the current and magnetic attraction and the motion. The resulting motion is the vibration of the armature bar 4. Coupled to the armature bar 4 is the tattoo needle 6. The motion of the armature bar 4 generates an axial vibration of the tattoo needle 6 that may be used to penetrate the skin and deposit colored ink.

Figure 2:
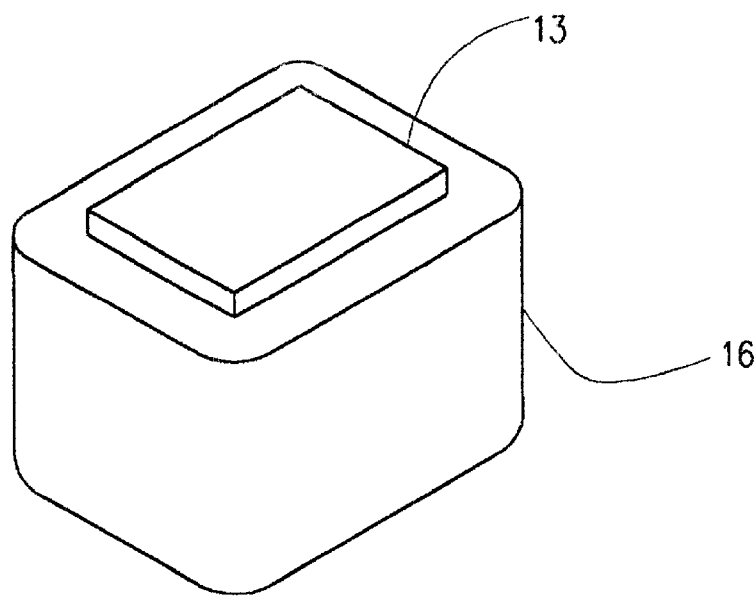
FIG. 2 shows a coil with a rectilinear core.
Figure 3:
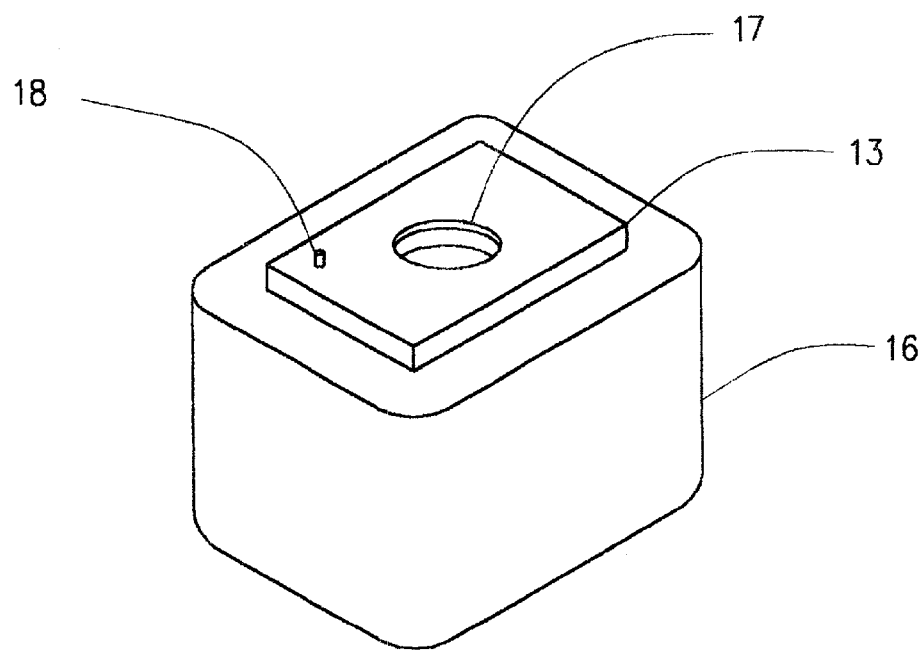
FIG. 3 shows the opposite end of a coil with a rectilinear core.

As shown in FIG. 2, the core 13 of each coil 1 has a rectilinear cross-section. Each edge of the cross-section is substantially at right angles to the adjacent sides, and the cross-section has four sides. The lengths of the opposite sides are equal, but the adjacent sides are not necessarily equal. The core is made from a magnetic material, usually iron or steel, and, having a rectilinear cross-section, therefore, producing a core that is a solid parallelepiped. The outer surface of the core 1 is wound with magnet wire 16. The edges of the core 13 can be radiused or chamfered so that the magnet wire 16 is not bent sharply as it goes over the edges. As shown in FIG. 3, a tapped hole 17 is located in the end of the core away from the armature to accept the fastener 3 that attaches the core 13 to the connector bar 2.

As the cores 13 are assembled to the connecting bar 2, it is preferred that an edge of the core cross-section is aligned to be parallel with the edge of the connecting bar 2. It is preferred that the length of the core cross-section aligned perpendicular to the long axis of the connecting bar be equal to the width of the connecting bar. Each core may incorporate features to facilitate the alignment, such as pins or ears that fit into matching holes in the connector bar. These features would also act to resist rotation of the core 13 while in service. A pin 18 is shown in FIG. 3 that would engage in a mating hole in the connector bar 2 to provide alignment and anti-rotation of the core 13.

Experimentation using the rectilinear core has shown the surprising result that the smoothness of the vibration of the tattooing machine is increased substantially when rectilinear cores are used in place of circular cross-section cores. This is reflected in the sensation felt by the operator during the tattooing operation. This is of substantial importance since the quality of the artistic result is directly related to the smoothness of the vibration sensation felt by the operator. This smoothness is a long sought goal among tattoo artists and was heretofore unavailable. This surprising result could not have been predicted due to the complexity of the interaction of the magnetic parts and the changing magnetic flux over the changing magnetic air gap.

After experiencing this result and in hindsight, it is suggested that the flux density in the air gap between the cores and the armature bar and the magnetic components has to change less and is more stable with the rectilinear cross-section core. This results in less disturbing acceleration in the armature bar during each cycle and minimizes disturbing changes from one cycle to the next. Since the flux density distributes itself to conform to the geometry of the excited cross-section, using similar cross-sections as set forth in this invention promotes fewer disturbances in the flux field as it passes between each core and the moving armature bar.

This invention may be extended to dual coil electromagnets in general.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and the descriptions herein are offered by way of example to facilitate comprehension of the invention and should not be construed to limit the scope thereof.

What is claimed is:

1. A handheld tattooing apparatus, comprising;

a frame, a position of which is constructed of magnetic material, a plurality of electrical coils, each coil having a core, each core having a rectilinear cross-section, each core having means for attachment to said frame in a position adjacent to said magnetic material, each coil being constructed of insulated electrical conducting wire, said wire being wound around said core, said wire being spatially fixed with respect to said core, an electrical power supply connected to said electrical conducting wire, said electrical power supply being capable of providing electrical power to said coils, an armature bar having a rectilinear cross-section and connected to said frame, said armature bar being located in a first position in proximity of the ends of said cores opposite said means for attachment with said frame, said armature bar being spring-biased away from said cores, said armature bar being attracted to said cores when said power supply provides electrical power to said coils, means for disconnecting said electrical power when said armature bar has moved to a second position, and reconnecting said electrical power when armature bar has returned to said first position, said second position being closer to said cores than said first position, a tattoo needle attached to said armature bar, said tattoo needle moving with the motion of said armature bar.

2. A handheld tattoo apparatus, according to claim 1, further comprising:

means for aligning said rectilinear cross-section of said core rotationally with the attachment surface of said connector bar.

3. A handheld tattoo apparatus, according to claim 2, wherein said means for aligning is a pin and mating hole.

4. A handheld tattoo apparatus according to claim 1, wherein said armature bar and said cores have substantially equal width dimensions, said width dimension being measured in the direction mutually perpendicular to the longitudinal axis of said armature bar and the longitudinal axes of said cores.

5. A handheld tattoo apparatus according to claim 1, wherein the cross-sectional dimensions of said armature bar and said cores are substantially equal.

* * * * *